(12) United States Patent
Davis et al.

(10) Patent No.: US 11,860,119 B2
(45) Date of Patent: Jan. 2, 2024

(54) SENSOR, SENSING SYSTEM AND SENSING METHOD BASED ON ANALYSIS OF RELAXATION TIME

(71) Applicants: Oxford University Innovation Limited, Oxford (GB); Universidade Estadual Paulista "Julio de Mesquita Filho"—UNESP, Centro São Paulo (BR)

(72) Inventors: Jason J. Davis, Oxford (GB); Paulo R. Bueno, Sao Paulo (BR)

(73) Assignees: OXFORD UNIVERSITY INNOVATION LIMITED, Oxford (GB); UNIVERSIDADE ESTADUAL PAULISTA "JULIO DE MESQUITA FILHO"—UNESP, Centro São Paulo (BR)

( * ) Notice: Subject to any disclaimer, the term of this patent is extended or adjusted under 35 U.S.C. 154(b) by 489 days.

(21) Appl. No.: 16/631,468

(22) PCT Filed: Jul. 16, 2018

(86) PCT No.: PCT/GB2018/052012
§ 371 (c)(1),
(2) Date: Jan. 16, 2020

(87) PCT Pub. No.: WO2019/016528
PCT Pub. Date: Jan. 24, 2019

(65) Prior Publication Data
US 2020/0209189 A1      Jul. 2, 2020

(30) Foreign Application Priority Data

Jul. 18, 2017   (GB) .................................... 1711543

(51) Int. Cl.
*G01N 27/414* (2006.01)
*G01N 33/543* (2006.01)
*G01N 27/22* (2006.01)

(52) U.S. Cl.
CPC ....... *G01N 27/4146* (2013.01); *G01N 27/221* (2013.01); *G01N 27/4145* (2013.01); *G01N 33/5438* (2013.01)

(58) Field of Classification Search
CPC ....................... G01N 27/4145; G01N 33/5438
See application file for complete search history.

(56) References Cited

U.S. PATENT DOCUMENTS

| 2004/0007740 A1 | 1/2004 | Abstreiter et al. |
| 2007/0210349 A1 | 9/2007 | Lu et al. |

(Continued)

FOREIGN PATENT DOCUMENTS

| EP | 2 017 609 A1 | 1/2009 |
| EP | 3 163 296 A1 | 5/2017 |

(Continued)

OTHER PUBLICATIONS

A. Mejia-Aguilar, Electrical Impedance Measurement Using Voltage/Current Pulse Excitation, XIX IMEKO World Congress, Fundamental and Applied Metrology, Sep. 6-11, 2009, Lisbon, Portugal, p. 662-67. (Year: 2009).*

(Continued)

*Primary Examiner* — Caitlyn Mingyun Sun
(74) *Attorney, Agent, or Firm* — Thomas|Horstemeyer, LLP (57) ABSTRACT

A sensing method is described. The sensing method comprises providing a time-dependent electrical signal across a conductive connection between first and second terminals of a sensor, the conductive connection capacitively coupled to an environment via a mesoscopic probe element having an (Continued)

electroactive surface for exposure to the environment, the conductive connection having an associated relaxation time. The method further comprises receiving a time-dependent response signal from the sensor. The method further comprises analysing the time-dependent response signal with respect to the time-dependent electrical signal. The method further comprises determining, based on the analysis, a change in the relaxation time, the change in the relaxation time being correlated with an interaction between the electroactive surface and a measurand of the environment. A computer-readable medium, a sensing system and a sensor are also described.

16 Claims, 8 Drawing Sheets

(56) References Cited

U.S. PATENT DOCUMENTS

| | | | | |
|---|---|---|---|---|
| 2009/0273356 | A1* | 11/2009 | Pampin | G01N 33/48728 324/693 |
| 2013/0158378 | A1* | 6/2013 | Berger | A61B 5/14546 438/49 |
| 2014/0175376 | A1* | 6/2014 | Avci | H01L 29/772 977/938 |
| 2016/0077047 | A1* | 3/2016 | Khamis | G01N 27/4146 506/3 |

FOREIGN PATENT DOCUMENTS

| | | |
|---|---|---|
| KR | 10-2001-0040559 A | 5/2001 |
| WO | 00/45160 A1 | 8/2000 |
| WO | 2005/000735 A2 | 1/2005 |
| WO | 2007/089550 A2 | 8/2007 |

OTHER PUBLICATIONS

HP Application Note 77-3, Measurement of Complex Impedance, Apr. 1, 1967, p. 1-12. (Year: 1967).*
Immitance_Wikipedia, the webpage recorded by Wayback Machine in 2016. (Year: 2016).*
A. Santos, Impedance-derived electrochemical capacitance spectroscopy for the evaluation of lectin-glycoprotein binding affinity, Biosensors and Bioelectronics, 2014(62), p. 102-05. (Year: 2014).*
B. Zhan, Graphene Field-Effect Transistor and Its Application for Electronic Sensing, Small, 2014 (10), p. 4042-65. (Year: 2014).*
Capacitor Impedance Calculator (Year: 2016).*
P.R. Bueno, The Mesoscopic Electrochemistry of Molecular Junctions, Nature, 2016, 6:18400, p. 1-11. (Year: 2016).*
Y. Chen, Nonequilibrium Tunneling Spectroscopy in Carbon Nanotubes, Physical Review Letters, 2009, 102, 036804, p. 1-4. (Year: 2009).*
International Search Report & Written Opinion for WO2019/016528 (PCT/GB2018/052012), dated Sep. 25, 2018, pp. 1-20.
UK Search Report for GB1711543.7, dated Jan. 12, 2018, pp. 1-4.
Paulo R. Bueno et al: "Quantum capacitance as a reagentless molecular sensing element", Nanoscale, vol. 9, No. 40, Sep. 18, 2017 (Sep. 18, 2017), pp. 15362-15370.
International Preliminary Report on Patentability for WO2019/016528 (PCT/GB2018/052012), dated Jan. 21, 2020, pp. 1-12.
European Examination Report for Application No. 18 745 701.5, dated Jul. 1, 2022, pp. 1-7.
Pandey Ashish et al: "Graphene-interfaced electrical biosensor for label-free and sensitive detection of foodborne pathogenic*E. coli*O157:H7", Biosensors and Bioelectronics 91 (2017) 225-231.
Office Action for Korean Patent Application 10-2020-7004728, dated May 22, 2023, pp. 1-21 (Translation Included).

* cited by examiner

SENSOR, SENSING SYSTEM AND SENSING METHOD BASED ON ANALYSIS OF RELAXATION TIME

CROSS-REFERENCE TO RELATED APPLICATIONS

This application is the National Stage of International Application No. PCT/GB2018/052012, filed Jul. 16, 2018, which claims the priority to GB 1711543.7, filed Jul. 18, 2017, which are entirely incorporated herein by reference.

TECHNICAL FIELD

The present disclosure concerns sensors, sensing systems and sensing methods, and in particular concerns density-of-states (DOS) sensitive sensors operable in the mesoscopic or nanoscale regime.

BACKGROUND

Sensors and sensing systems are required to detect many measurands. When the object to be detected is very small, for example when a molecule is to be detected, extremely responsive or sensitive sensors are required. There is a considerable need for sensing technology for detecting measurands and analytes at the mesoscopic level.

It is an object of embodiments of the invention to at least mitigate one or more of the problems of the prior art.

SUMMARY

According to an aspect of the invention a sensing method is provided. The method comprises providing a time-dependent electrical signal across a conductive connection between first and second terminals of a sensor. The conductive connection is capacitively coupled to an environment via a mesoscopic probe element having an electroactive surface for exposure to the environment. The conductive connection has an associated relaxation time. The method further comprises receiving a time-dependent response signal from the sensor. The method further comprises analysing the time-dependent response signal with respect to the time-dependent electrical signal. The method further comprises determining, based on the analysis, a change in the relaxation time. The change in the relaxation time being correlated with an interaction between the electroactive surface and a measurand of the environment.

The density-of-states (DOS) of a system describes the number of states per interval of energy at each energy level. The disclosed sensing method allows for highly sensitive DOS-based sensing which can readily be integrated into a highly convenient microprocessor/microelectronic format. The sensor described herein is analogous to a DOS-sensitive field effect transistor and can be referred to as a DO2S-FET in what follows. The DO2S-FET is conveniently modifiable with receptors in generating highly effective sensors for any target or measurand of interest, where the responsive DOS is only accessible through time-dependent measurements such as alternating current (AC) or pulsed electric methodologies. This sensor capability integrates neatly within Complementary-Metal-Oxide-Semiconductor (CMOS) technology (which operates exclusively in the direct current—DC—regime). The sensor and sensing system can be miniaturised and are highly scalable.

The word "mesoscopic" as used herein can be taken to mean a size between the size of a quantity of atoms and a few micrometres. The lower limit of a "mesoscopic" range would be understood to mean a size of a few atoms, and the upper limit of a mesoscopic range would be understood to mean a microscale size (that is, at the micrometre level). Whereas the properties of a macroscopic object are derived from the average properties of the macroscopic object's constituent materials, a mesoscopic object is affected by fluctuations around the average and is subject to quantum mechanical effects. Mesoscopic may be understood to mean, for example, at the nanoscale. A mesoscopic probe element as described herein is therefore a feature, probe, or element, which may comprise at least one length, breadth, width or other dimension which is mesoscopic. For example, a mesoscopic probe element may comprise a quantum dot or a titanium oxide nanotube. A mesoscopic probe element as described herein may therefore be of an appropriate nanometre scale and have an accessible DOS.

The word "electroactive" as used herein is understood to describe a material that is electrically responsive. In particular, an electroactive surface comprises a surface which is electrically responsive to an interaction which can alter the DOS of the surface, such as an interaction with a molecule or a photon.

The "environment" as described herein is taken to mean the environment of the mesoscopic probe element (as it is the interactions between an electroactive surface of the probe element and a measurand of the environment that is to be detected). The environment may be a liquid, a gas, a plasma or anything else. For example, the sensor may be provided in a vacuum and used to detect electromagnetic radiation.

The "relaxation time" as used herein refers to the response of the sensor to a time-dependent electrical signal and would be readily understood by the person skilled in the art. The relaxation time is dependent on the impedance and the capacitance $C_\mu$ of the circuit and, as will be shown below, can vary in the presence of a measurand which alters the density of states at the interface between the electroactive surface of the sensor and the environment.

A "terminal" as used herein refers to a point at which the sensor can connect to a circuit. For example, the conductive connection referred to herein may comprise a conducting wire, and a terminal may be understood to mean an end of that wire (and a mesoscopic probe element may comprise a coating on the wire). As an alternative, a single electrode or body may be provided and the first and second terminals may therefore be taken to mean the points at which said electrode or body is connected to a circuit (and a mesoscopic probe element may comprise a mesoscopic layer upon the electrode or body).

The time-dependent electrical signal may be considered an example of an input signal. The time-dependent response signal may be considered as an example of an output signal. Accordingly, the analysing step of the method described above may be thought of as an analysis of an output signal with respect to an input signal.

The time-dependent electrical signal may be an alternating current. An alternating current is advantageous as it allows for a time-dependent response signal to be analysed against a predictable time-dependent electrical signal. Further advantageously, the frequency of the alternating current may be selected so as to optimise sensitivity of the sensing system to a particular measurand of interest.

The time-dependent electrical signal may be an electrical pulse.

Receiving a signal, be it a time-dependent electrical signal or a time-dependent response signal, may comprise receiving as a result of a measurement, such as with an ammeter or a voltmeter.

Analysing the time-dependent response signal with respect to the time-dependent electrical signal may comprise determining a phase difference between the time-dependent response signal and the time-dependent electrical signal. Determining a change in the relaxation time may comprise determining that a change in the relaxation time has occurred based on the phase difference.

Analysing the time-dependent response signal with respect to the time-dependent electrical signal may comprise determining an immittance function of the sensor from the time-dependent electrical signal and the time-dependent response signal. The immittance function may indicate the impedance and/or admittance of the sensor. For example, one may consider the ratio of the current to the voltage, or may consider the ratio of the voltage to the current.

Analysing the time-dependent response signal with respect to the time-dependent electrical signal may comprise determining the impedance of the sensor from the ratio of the time-dependent electrical signal to the time-dependent response signal.

Analysing the time-dependent response signal with respect to the time-dependent electrical signal may comprise determining the capacitance of the sensor using impedance-derived capacitance spectroscopy.

The method may further comprise determining a concentration of the measurand in the environment.

The interaction may comprise an electronic interaction between the electroactive surface and the measurand. The interaction may comprise a molecular binding event. The interaction may comprise a photon-electron interaction.

The mesoscopic probe element may comprise a mixed valence oxide. The mesoscopic probe element may comprise graphene oxide. The mesoscopic probe element may comprise titanium dioxide.

The mesoscopic probe element may have at least one dimension having a size of less than 20 nanometres. The dimension may have a size of less than 15 nanometres, or less than 10 nanometres.

The conductive connection may comprise gold.

A computer-readable medium is provided. The computer-readable medium has instructions provided thereon which, when read by a processor and/or other processing means, cause the processor and/or other processing means to implement a method according to an embodiment of the invention as described herein.

A sensing system is provided. The sensing system comprises signal generating means; and a sensor, wherein the signal generating means is arranged for providing a time-dependent electrical signal to the sensor. The sensor comprises a mesoscopic probe element having an electroactive surface for exposure to an environment. The sensor further comprises first and second terminals connectable to the time-dependent electrical signal. The first terminal is coupled with the second terminal via a conductive connection such that no biasing potential exists between the first and second terminals. The conductive connection is capacitively couplable to the environment via the mesoscopic probe element, such that an interaction between the electroactive surface and a measurand in the environment is correlated with a change in relaxation time of the conductive connection. The sensing system further comprises signal analysing means for analysing the time-dependent electrical signal with respect to a time-dependent response signal from the sensor to identify a change in the relaxation time of the conductive connection.

The sensor may further comprise a body which comprises the first and second terminals. For example, the body may comprise a single electrode or contact, on which the mesoscopic probe element may be mounted or affixed. Advantageously, the use of a single body or electrode improves the sensitivity/responsiveness of the sensor and sensing system as there is no need to correct for noise from further electrodes.

The conductive connection may comprise gold.

The mesoscopic probe element may comprise graphene oxide or titanium dioxide. The mesoscopic probe element may comprise a quantum dot or a collection of quantum dots. The mesoscopic probe element may comprise one or more titanium nanotubes or nanowires.

The mesoscopic probe element may have at least one dimension having a size of less than 20 nanometres. The at least one dimension may have a size of less than 15 nanometres, or less than 10 nanometres.

The interaction may comprise an electronic interaction between the electroactive surface and the measurand. The interaction may comprise a molecular binding event. The interaction may comprise a photon-electron interaction.

A sensor is provided. The sensor comprises a mesoscopic probe element having an electroactive surface for exposure to an environment. The sensor further comprises first and second terminals connectable to a time-dependent electrical signal. The first terminal is coupled with the second terminal via a conductive connection such that no biasing potential exists between the first and second terminals. The conductive connection is capacitively couplable to the environment via the mesoscopic probe element, such that an interaction between the electroactive surface and a measurand in the environment is correlated with a change in relaxation time of the conductive connection.

BRIEF DESCRIPTION OF THE DRAWINGS

Embodiments of the invention will now be described by way of example only, with reference to the accompanying figures, in which.

Throughout the description and the drawings, like reference numerals refer to like parts.

DETAILED DESCRIPTION OF EMBODIMENTS OF THE INVENTION

Figure 1:
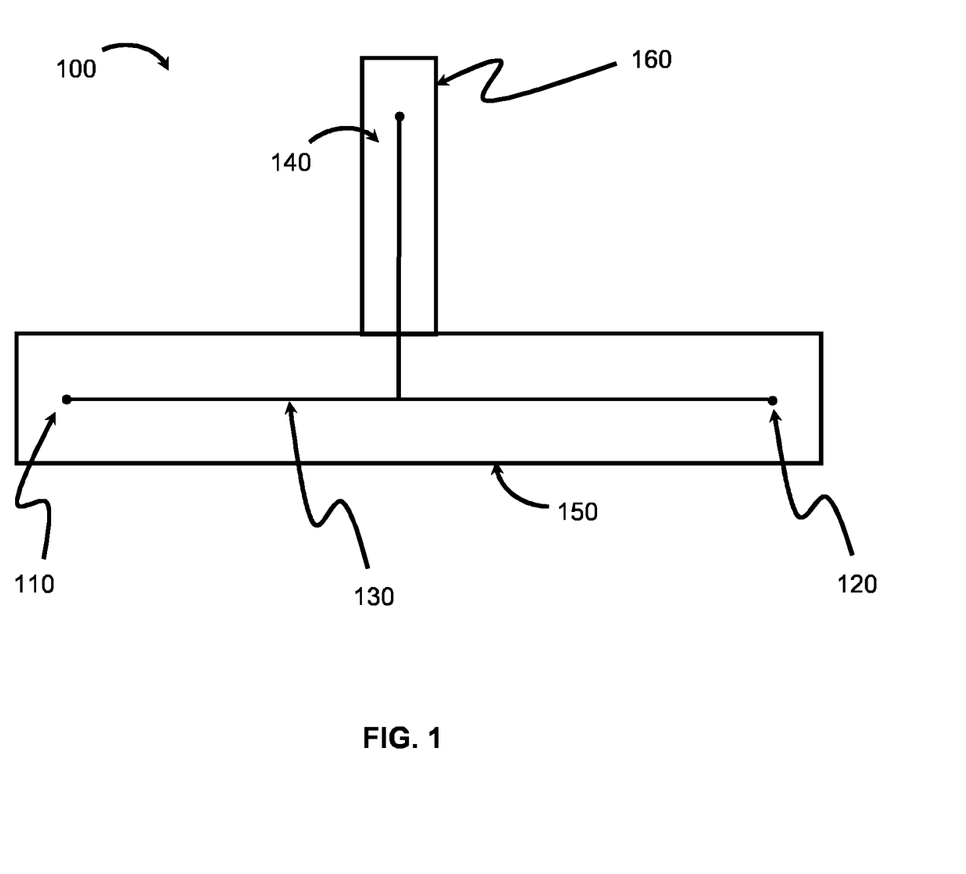
FIG. 1 illustrates a sensor according to an embodiment of the invention.

FIG. 1 is a diagram of a sensor 100 in accordance with an embodiment of the invention. A sensor 100 comprises a first terminal 110 and a second terminal 120 coupled via a conductive connection 130. In the embodiment shown in FIG. 1, the first terminal 110 and the second terminal 120 are provided on the same body/electrode 150, and in this embodiment the electrode 150 comprises the first terminal 110, the second terminal 120 and the conductive connection 130. However, it is to be understood that the first terminal 110 and the second terminal 120 may be provided on separate bodies/electrodes such that they are physically distinguishable from one another. A mesoscopic probe element 140 is capacitively coupled to the conductive connection 130, as will be explained in further detail below.

The sensor 100 may be considered as a Density-of-State sensitive field effect transistor (DO2S-FET). A field effect transistor (FET) is a transistor in which most current is carried along a channel between source and drain terminals of the FET, the channel having an effective resistance controllable by a transverse electric field. In particular, the source terminal is a terminal through which charge carriers (electrons) enter the channel, the drain terminal is a terminal through which the charge carriers leave the channel, and a gate terminal modulates the channel conductivity. By applying a voltage to the gate terminal, one can control the current at the drain terminal. A classical FET device operates based on a direct current-voltage (DC) response; by applying a potential difference between the source and drain terminals an electric current is permitted to flow in the channel, subject to moderation by the gate potential, otherwise the FET is said to be in an equilibrium condition.

For the sensor 100 (which may also be referred to as a DO2S-FET in what follows), the first terminal 110 and the second terminal 120 may be considered as source and drain terminals of a transistor. However, as opposed to having a direct current (DC) biasing potential applied across the first and second terminals, the first and second terminals (110, 120) may be considered as at equilibrium condition (when no current is applied) such that the potential difference between the first and second terminals is substantially zero. In such a scenario, the resistive and capacitive properties of the channel/conductive connection may be probed using a time-dependent electrical signal, such as an alternating current or an electrical pulse. The relaxation time of the sensor can be tailored during fabrication by doping or adjusting the thickness of the body.

The conductive connection 130 is depicted by a solid line in FIG. 1, although the skilled person would appreciate that the conductive connection may be any suitable conductor and of any suitable thickness. The conductive connection between the first terminal 110 and the second terminal 120 is capacitively coupled to an environment via the mesoscopic probe element 140.

As the mesoscopic probe element 140 has at least one mesoscopic dimension, the quantum capacitance $C_q$ varies as a function of the density-of-states occupancy of the probe element 140. In this way, and as will be explained in further detail below, any interaction between the mesoscopic probe element 140 and a measurand which results in a change in the electron density of states of the mesoscopic probe element 140, will have an influence on the capacitive and resistive properties of the sensor 100 (and therefore the relaxation time of the sensor 100), as probed by a time-dependent electrical signal. Accordingly, an electroactive surface 160 of the mesoscopic probe element 140 may be considered to function as a gate terminal of the DO2S-FET architecture, as emphasised by the solid line connecting the conductive connection 130 to the mesoscopic probe element 140 in FIG. 1.

Figure 2:
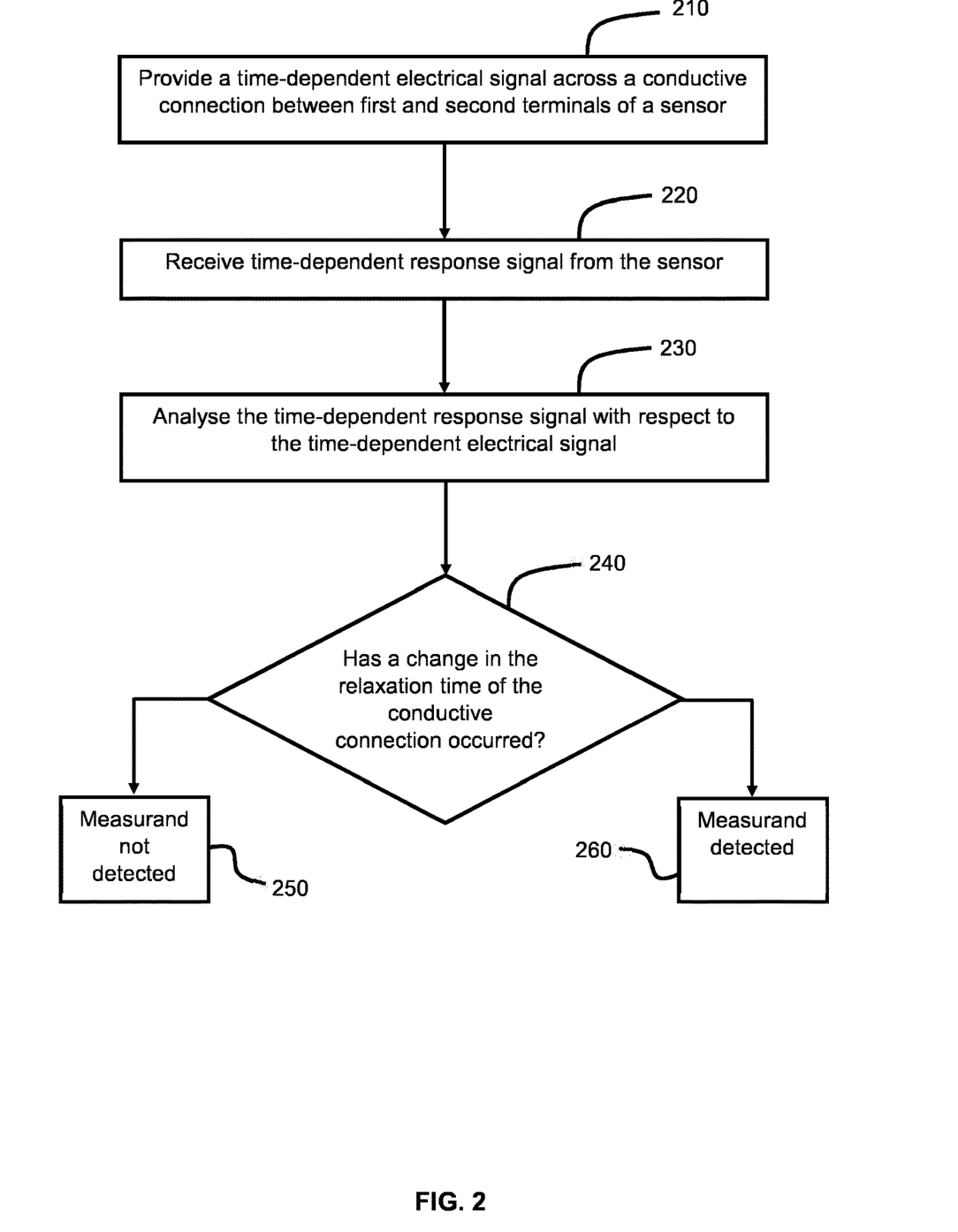
FIG. 2 shows a flowchart of a sensing method according to an embodiment of the invention.

FIG. 2 is a flowchart of a sensing method which may be carried out using, for example, the sensor 100 of FIG. 1.

At step 210, a time-dependent electrical signal is provided across the conductive connection 130 between the first terminal 110 and the second terminal 120. For example, the first terminal 110 and the second terminal 120 may be connected to an alternating current/voltage or connected to a pulsed electrical signal. As has been explained above, the conductive connection 130 of the sensor 100 is capacitively coupled to an environment via a mesoscopic probe element 140 of the sensor, the mesoscopic probe element 140 having an electroactive surface 160 for exposure to the environment. The conductive connection also has an associated relaxation time/RC response.

The electrical signal may be any suitable electrical signal having a time-varying profile. For example, the electrical signal may be an alternating current/voltage, or may be an electrical pulse.

At step 220, a time-dependent response signal is received from the sensor 100. The time-dependent response signal may comprise an alternating current/voltage or an electrical pulse. The time-dependent response signal depends on the time-dependent electrical signal provided to the sensor 100 and the response characteristics or relaxation time of the sensor 100.

At step 230, the time-dependent response signal is analysed with respect to the time-dependent electrical signal.

For example, the analysis may comprise determining a phase difference between the time-dependent response signal and the time-dependent electrical signal.

Analysing the time-dependent response signal with respect to the time-dependent electrical signal may comprise determining an immittance function of the sensor from the time-dependent electrical signal and the time-dependent response signal. Analysing may comprise determining the impedance of the sensor 100 from the ratio of the time-dependent electrical signal to the time-dependent response signal. Analysing may comprise determining the capacitance of the sensor 100 using any suitable method such as impedance-derived capacitance spectroscopy.

At step 240, it is determined, from the analysis at step 230, whether a change in the relaxation time of the sensor has been detected, a change in the relaxation time being correlated with a change in the density of states of the surface 160 of the mesoscopic probe element 140. A change in density of states can occur from an interaction between the electroactive surface 160 of the mesoscopic probe element 140 and a measurand of the environment. For example, when the analysing at step 240 comprises determining a phase difference between the time-dependent response signal and the time-dependent electrical signal, determining whether a change in the relaxation time of the sensor has been detected may comprise determining that a change in the relaxation time has occurred based on the phase difference.

If a determination is made, at step 240, that a change in relaxation time has not occurred, then a determination is made that a measurand has not been detected (250). If a determination is made, at step 240, that a change in relaxation time has occurred, then a determination is made that a measurand has been detected (260).

Figure 3:
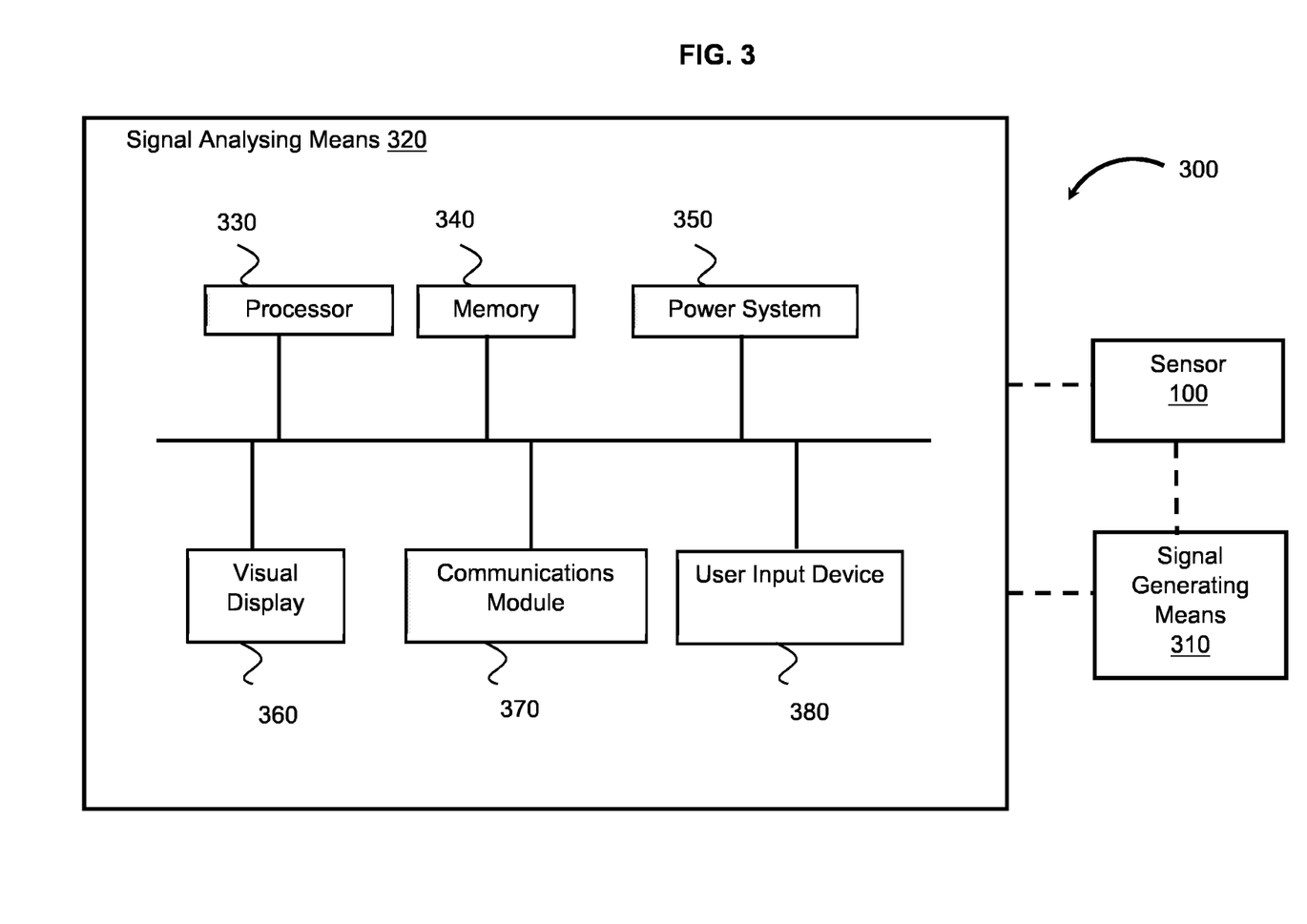
FIG. 3 shows a sensing system according to an embodiment of the invention.
Figure 4:
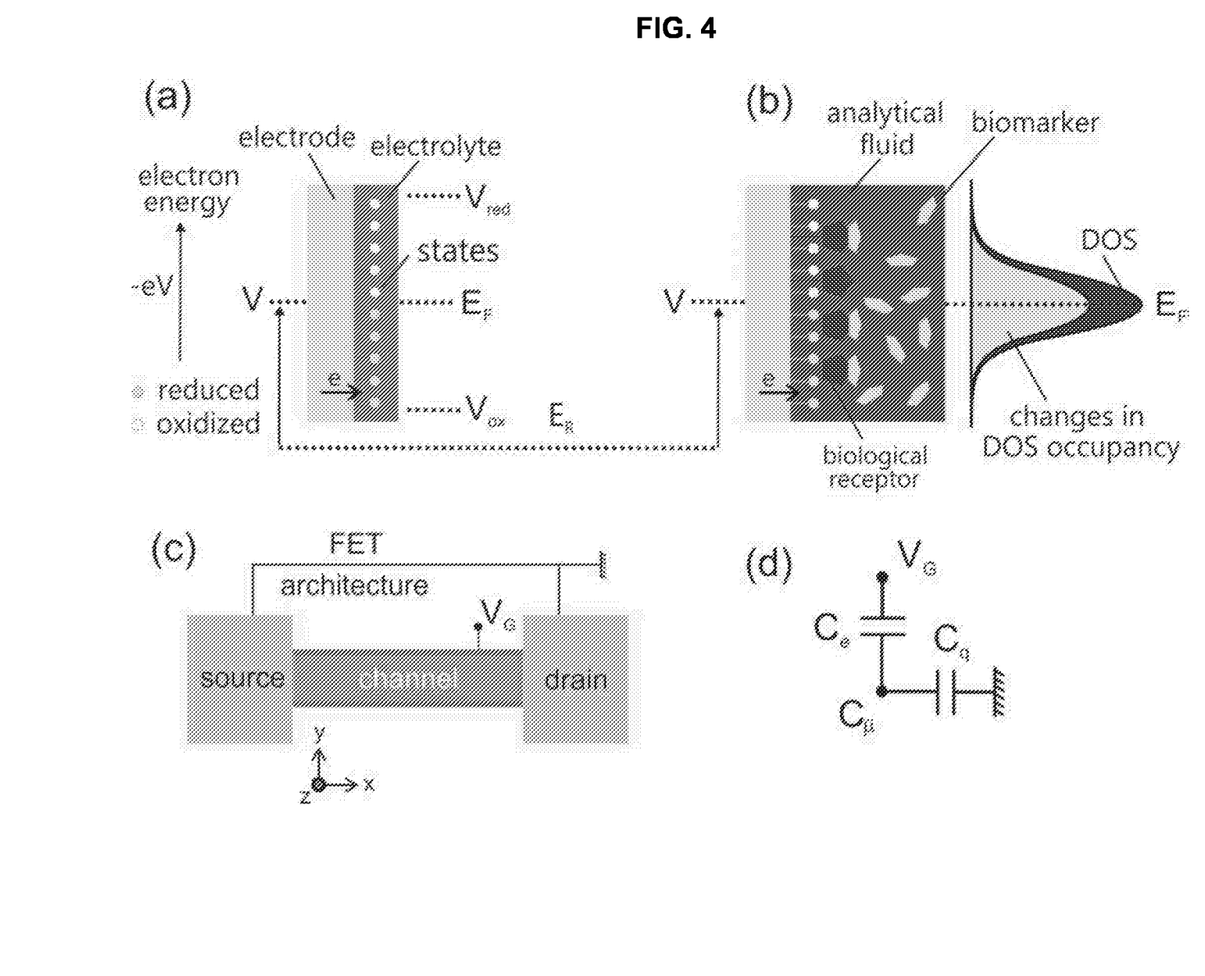
FIG. 4a shows a schematic illustration of the energy levels for an electrochemical junction composed of an electrode and a generic electroactive system immersed in electrolyte.
FIG. 4b is similar to FIG. 4a and with integrated biological receptors within a mixed junction also containing electroactive states.
FIG. 4c illustrates an architecture of a Field Effect Transistor (FET) according to an embodiment of the invention.
FIG. 4d shows the FET associated equivalent circuit that governs behaviour when only gate voltage is varied under equilibrium conditions.
Figure 5:
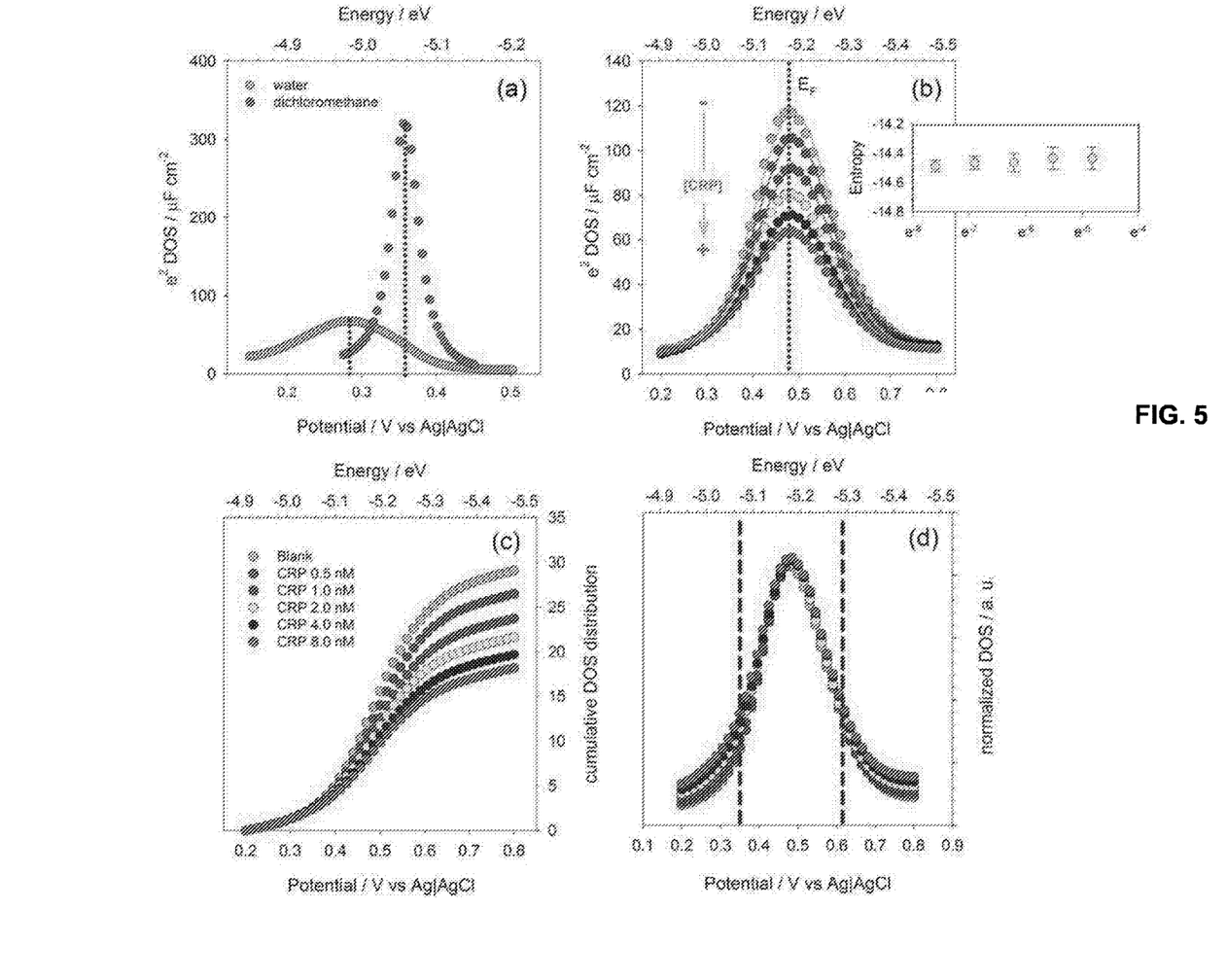
FIG. 5a is a graph showing the effect of environment dielectric on resolved density-of-states (DOS) distribution of an electroactive layer according to an embodiment of the invention.
FIG. 5b is a graph showing the responsiveness of redox DOS to molecular recognition within a mixed redox switchable and antibody constrained film.
FIG. 5c is a graph showing the cumulative distribution function of electronic states as a function of electrode potential.
FIG. 5d is a graph showing the density-of-state function of FIG. 5b normalised for the total state occupancy at each target concentration.

FIG. 3 is a block diagram of a sensing system 300 in accordance with an embodiment. The sensing system comprises a sensor 100, which may correspond to the sensor 100 of FIG. 1. The sensing system further comprises a signal generating means 310 and a signal analysing means 320. Other architectures to that shown in FIG. 3 may be used as will be appreciated by the skilled person. For example, the signal generating means 310 and the signal analysing means 320 may be provided in the same device or controller.

As described above in relation to FIG. 1, the sensor 100 comprises a first terminal 110 and a second terminal 120 coupled via a conductive connection 130, which in turn is capacitively coupled to an environment via a mesoscopic probe element 140 having an electroactive surface in contact with the environment. The properties of the conductive connection 130 including the capacitance, impedance and the relaxation time of the conductive connection 130, can be explored with the use of a time-dependent electrical signal. In this way it may be determined whether or not an interaction has occurred between the electroactive surface and a measurand of the environment.

Signal generating means 310, which in the present embodiment comprises a signal generator, is configured to send a time-dependent electrical signal such as an alternating current or an electrical pulse, to the sensor 100. The signal generating means 310 is also configured to communicate the generated signal to the signal analysing means 320 for analysis.

The signal analysing means 320, which in the present embodiment comprises a signal analyser, is configured to receive a time-dependent response signal from the sensor 100 and to receive an indication of the sent time-dependent electrical signal from the signal generator 310.

Referring to the figure, the signal analysing means 320 comprises a communications module 370 for receiving information from the sensor 100 and the signal generating means 310. The communications module 370 may be in any suitable form. For example, the communications module 270 may comprise one or more measurement apparatuses for monitoring or measuring the time-dependent electrical signal sent from the signal generating means 310 and the time-dependent response signal from the sensor 100. For example, the communications module 370 may comprise one or more ammeters and/or voltmeters for directly measuring the response signal from the sensor 100.

In the present embodiment, the signal analysing means further comprises processing means in the form of a processor 330. A storage means in the form of a memory 340, and a powering means in the form of a power system 350.

The processing means 330 is configured to receive data, access the memory 340, and to act upon instructions received either from said memory 340, from communications module 370, or from one or more virtual or dedicated user input devices 380. The processor 330 is arranged to receive a time-dependent response signal from the sensor 100. The processor 330 is arranged to analyse the time-dependent response signal with respect to the time-dependent electrical signal. The processor 330 is arranged to determine, from the analysis, whether a change in the relaxation time of the conductive connection of the sensor 100 has occurred. This may be by, for example, determining that a change in phase difference between the time-dependent electrical signal and the time-dependent response signal has occurred. The processor 330 may be arranged to determine, from the analysis, a concentration or amount of the measurand in the environment about the sensor 100.

The processor 330 is arranged to indicate to visual display 360 whether or not a change in the relaxation time has occurred.

The signal generating means 310 may comprise similar components to the signal analysing means 320. In some embodiments, the signal generating means 310 and the signal analysing means 320 may be integrated into a single controller which controls both the signal generation and the signal analysis.

How the sensor 100 functions will become more apparent to the reader from the following, in which the principles of DOS-based sensing are explained and demonstrated, with reference to FIGS. 4 to 8.

A molecular junction immersed into an electrolyte generates a capacitance that is largely modelled by classical means using double layer interfacial capacitance models. The simplest model that works adequately at high (>0.1 M) ionic strength is that presented by Gouy-Chapman where the double layer capacitance (per unit of area) is given by $C_i=\varepsilon_r\varepsilon_O\kappa$, wherein $\varepsilon_r$ is the relative static permittivity (generally referred to as the dielectric constant) of the material, $\varepsilon_O(\sim 8.85\times 10-12 \text{ F m}^{-1})$ is the dielectric constant or dielectric permittivity of vacuum and $\kappa$ is the inverse of Debye length ($L_D=1/\kappa$), classically given by $\kappa=[(2e^2N)/(\varepsilon_r\varepsilon_O k_B T)]^{1/2}$. N denotes the density (molar concentration) of ionic charge (positive or negative) in the bulk of the electrolyte, $k_B$ is the Boltzmann constant, and T absolute temperature. Nonetheless this, and any other presented double layer model, fails when electronic states of an adsorbate mix with electrode states. This is the case, for instance, with electroactive molecular films wherein the innate presence of quantized and redox accessible electronic sites generates additional capacitive effects (usually engrained within what is described as a "pseudo capacitance"). This additional capacitive effect is associated with the charging of localized chemical states in a way somewhat detached from pure electrostatics. Under such circumstances, both ionic and electronic contributions must be considered in a combined electrochemical capacitance $C_{\bar{\mu}}$ which includes a (density-of-states based) consideration of Thomas-Fermi screening [$(1/C_{\bar{\mu}}=1/C_e+1/C_q)$, where electrostatic ($C_e$) and quantic ($C_q$) capacitance terms contribute] and $\kappa=(C_{\bar{\mu}}/\varepsilon_r\varepsilon_O)^{1/2}$.

Capacitive contributions from both ionic (distinguishable particles) and electronic (indistinguishable particles) sources are engrained in experimentally resolvable $C_{\bar{\mu}}$. In the former case, a Boltzmann approximation can be assumed for the occupancy such that $N\propto\exp[\bar{\mu}/\kappa_B T]$. For indistinguishable (electronic) particles $N\propto(1+\exp[\bar{\mu}/\kappa_B T])^{-1}$. If the former dominates then $\kappa=[(2e^2 N)/(\varepsilon_r\varepsilon_O\kappa_B T)]^{1/2}$ is recovered from $\kappa=(C_{\bar{\mu}}/\varepsilon_r\varepsilon_O)^{1/2}$. Accordingly, the classic double layer phenomenology is thus only a particular form of $C_{\bar{\mu}}$ arising specifically when charging at the interface is exclusively ionic in origin. In situations where there is a significant accessible nanoscale electronic density of states (DOS), this dominates in measured $C_{\bar{\mu}}$ and the electrical field screening is primarily governed by electrons.

Under such circumstances, one can directly relate the $1/C_{\bar{\mu}}$ and its relationship to electronic occupation of states, to energy storage (E=qV and where q=Ne is the charge; e is the elementary electron charge) as expressed by $$E = \frac{q^2}{2C_{\bar{\mu}}} = \sum \varepsilon_i + \frac{q^2}{2C_e} \quad (1)$$

wherein $\Sigma\varepsilon_i$ is the sum of individual occupied state energies, $\varepsilon_i$. If the occupation of states is environmentally responsive then the associated experimentally resolved $C_{\bar{\mu}}$, which directly reports on DOS occupation, responds likewise.

One can experimentally measure $C_{\bar{\mu}}$ using a sensor 100 such as that shown in FIG. 1 and relate the capacitance directly to quantised occupancy according to $N\propto(1/e^2)\int C_{\bar{\mu}}dV$, wherein $\Delta V=\int_{v_i}^{v_f}dV$ accounts for the potential window being scanned. $C_{\bar{\mu}}$ is recorded at a fixed frequency low enough for there to be no kinetic limitations.

FIG. 4a is a schematic illustration of the energy levels for an electrochemical junction composed of an electrode (yellow) and a generic electroactive system immersed in electrolyte (blue). The electrode may correspond to the conductive connection and/or mesoscopic probe element described above in relation to FIGS. 1 to 3, and the electrolyte may correspond to the environment. The redox reaction free energy is defined as $\Delta G_r=e(V-V_r)=E-E_F$, where e is the electron charge, and V is the electrode over potential. The expression $V_{red}-V_{ox}$ corresponds to the difference between fully reduced and oxidised states of the junction whereas $E_R$ is the reference energy level. FIG. 4b is equivalent to FIG. 4a with integrated biological receptors within a mixed junction also containing electro-active states. When a target biomarker is recruited the occupation of the electronic states changes and the experimentally measured change in interfacial energy transduces this through its effect on the film localized DOS. FIG. 4c denotes the equivalent operation of a field effect transistor (FET) operating under equilibrium conditions, wherein the electrochemical potential of the left- and right-hand electrodes are equal. In a classical FET, the electron density in the channel/conductive connection between the source and drain terminals (first and second terminals) changes as the gate voltage changes. In much the same way, the conductive properties of the conductive connection 130 of the sensor 100 of FIG. 1 are altered when an interaction occurs between the mesoscopic probe element 140 and a measurand of the environment. FIG. 4d demonstrates the FET associated equivalent circuit that governs behaviour when only gate voltage ($V_G$) is varied under equilibrium conditions, wherein the first and second terminals (source and drain terminals) are poised at the same potential. In such a configuration, the equivalent capacitance is the electrochemical capacitance, measured as $C_{\bar{\mu}}=C_e C_q/(C_e+C_q)$.

FIG. 5a is a graph showing the effect of environment dielectric on resolved DOS distribution of an electroactive molecular layer; solvent polarity tunes both the DOS energetic dispersion and the associated Fermi energy (dotted lines). Notably, the integrated accessible electron density is not affected (being here a substantially constant ~$10^{19}$ states per $cm^{-3}$). FIG. 5b is a graph showing the responsiveness of redox DOS to molecular recognition within a mixed redox switchable and antibody constrained film (see FIG. 4b). The inlay in FIG. 5b shows the invariance in both Fermi energy of the junction (~0.49V versus Ag|AgCl chemical reference) and state dispersion with C-Reactive Protein target concentration. FIG. 5c shows the cumulative distribution function [$\Delta N[target]\propto(1/e^2)\int C_{\bar{\mu}}dV$] of electronic states as a function of electrode potential, where the DOS occupancy changes as directly reported. N varies as a function of target protein concentration such as $\Delta N\propto\Delta(dN/dE)[target]$. FIG. 5d is a graph showing the density of state function data of FIG. 5b normalized for the total state occupancy at each target concentration ($\Delta N_t[target]$; obtained by integration of the DOS across all relevant energies). The superposition of the resulting plots confirms that the energetic change associated with occupancy change, $\Delta E/\Delta N_t[target]=(e^2/C_{\bar{\mu}})$, is a constant. All values/curves obtained represent means across triplicate measurements.

As shown in FIG. 5a, a change in local dielectric constant translates into a resolved DOS energetic redistribution without a change in total state occupancy [$\Delta N_t=(1/e^2)\int_{-\infty}^{\infty}C_{\bar{\mu}}(V)dV$, as expressed by the total area of the normal DOS distribution function]. A molecular binding event, however (such as that occurring at a neighbouring receptive site) triggers a resolved change in DOS occupation (FIG. 5b). One can seek to distinguish between these two environmental triggers by looking at the DOS shape (that follows a normal distribution) and its associated energetic spread as expressed through $S[dN/dE]=\ln\sigma_g\sqrt{2\pi e_n}$ (the entropy function of the normal DOS distribution), where $e_n$ is the base of natural logarithms and $\sigma_g$ the standard deviation. In the case of dielectric change, there is a clearly resolved change in dispersion (FIG. 5a). The effects of a local binding event are different in that there is an associated change in chemical potential resolvable through DOS occupation or measured $C_{\bar{\mu}}$ without change in electronic dispersion (inset FIG. 5b) or in Fermi energy.

Figure 6:
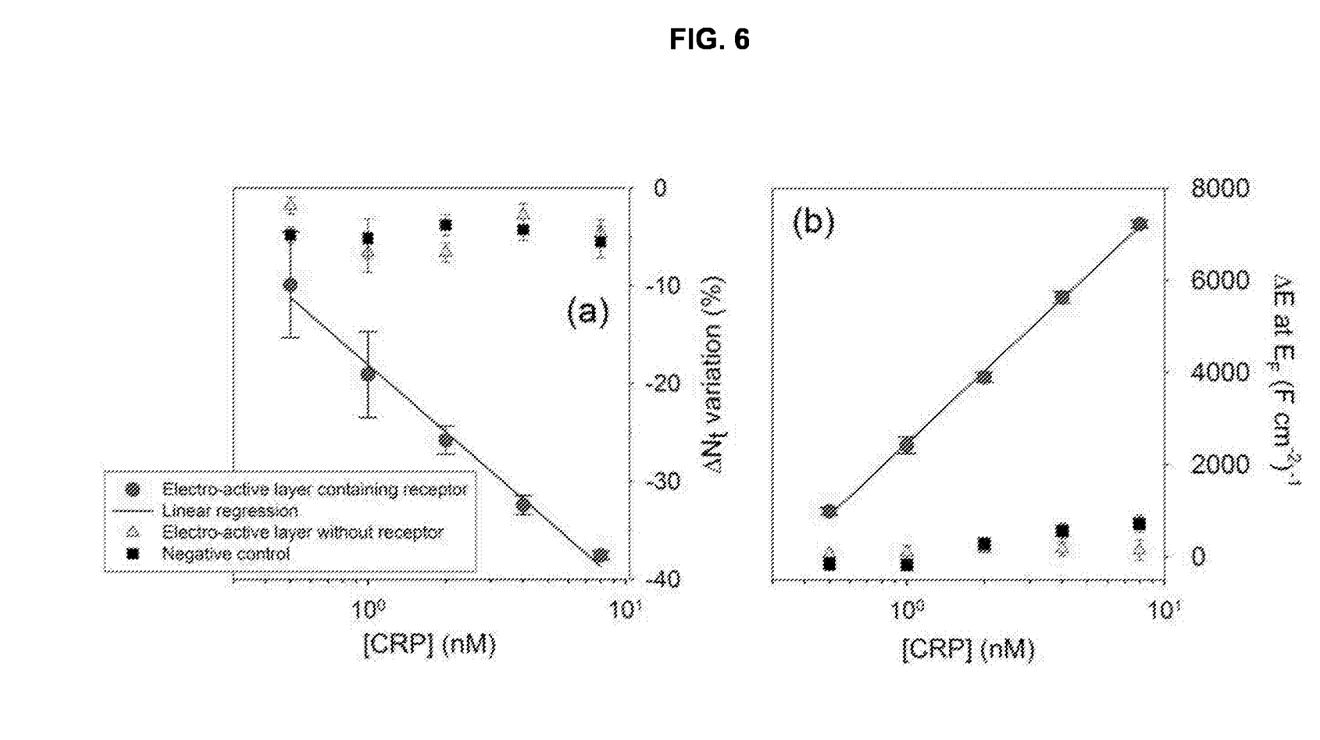
FIG. 6a shows the linear relationship between the variation of total electron density.
FIG. 6b shows analytical curves generated using local recognition induced energy change as resolved at a single potential.

From Equation (1) the variation in energy per number of particles (the energy/chemical potential change associated with DOS occupancy change) is $dE/dN=N(e^2/C_{\bar{\mu}})$, from which the associated change in energy and capacitance are quantified as $\Delta E=(e^2 C_{\bar{\mu}})$ and $C_{\bar{\mu}}/N=e^2(DN/dE)$, respectively. If one normalizes the experimentally measured electrochemical capacitance change (which is proportional to the DOS) across target binding concentrations for the total number of states $\Delta N_t[target]$, that is $\Delta C_{\bar{\mu}}/\Delta N_t[target]=[e^2(dN/dE)]$ the responses collapse to constant $e^2(dN/dE)$ value (FIG. 5d). Ultimately this confirms that a neighbouring molecular recognition and associated chemical potential change perturbs only occupancy of the DOS (without a change in the entropy associated with electronic states occupancy, in the present example). This is especially notable close to the electrode Fermi level, wherein the relationship is linear (as expected for an idealised two-dimensional electron gas, where $e^2/C_{\bar{\mu}}$ is constant). In summary, the electronic DOS, presented by a redox molecular film, responds to a neighbouring molecular recognition such that the resolved electronic charge $\Delta N$, is proportional to the target/analytic concentration. This is illustrated in FIG. 6, in which the target is C-reactive protein (CRP).

FIG. 6a is a graph showing the linear relationship between the variation of total electron density obtained from DOS integration $(1/e^2)\int_{-\infty}^{\infty} C_{\bar{\mu}}(V)dV$ in the entire interval of potential shown in FIG. 5d as a function of target CRP concentration at a redox active SAM-anti-CRP modified gold electrode. The redox unit acts as a mesoscopic probe element 140. The resolved redox DOS is unresponsive both to an equivalent concentration of a negative control (here Fetuin-A) and to CRP in the absence of a specific antibody receptor (yellow triangles). From the specific response, binding affinities are readily resolved from subsequent fitting to a Langmuir isothermal model; here $3.2\pm4\times10^8$ mol$^{-1}$ L, comparable to that obtained by other methods for the same interfacial immuno-complexation. It is possible to generate analytical curves (FIG. 6b) using the local recognition induced energy change ($\Delta E$), as resolved at a single potential, 0.49 V versus Ag|AgCl, the Fermi energy ($E_F$) of the junction. Energy and occupancy are anti-correlated. The error bars represent standard deviation across three independent receptive junctions.

This DOS based sensing is, of course, a general principal that the skilled person would appreciate can be readily extended to the selective detection of other markers alternatively using specific interfacial chemistries (see FIG. 7).

Figure 7A:
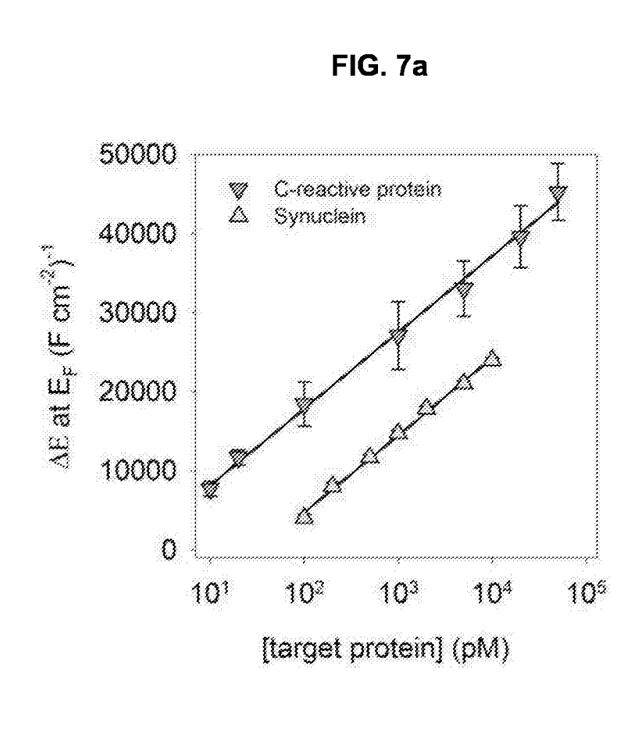
FIG. 7a shows analytical curves obtained by plotting variation of the energy of the accessible interfacial states at their fixed Fermi energy for clinically relevant markers.
Figure 7B:
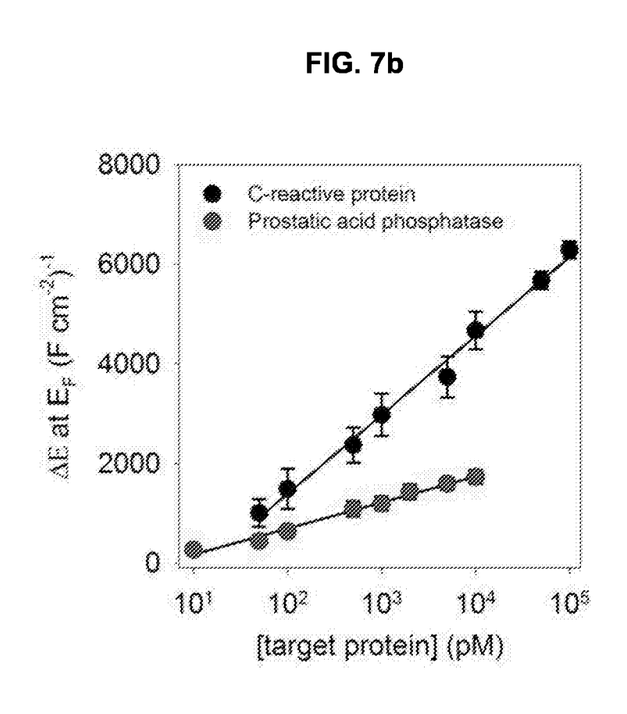
FIG. 7b shows analytical curves obtained by plotting variation of the energy of the accessible interfacial states at their fixed Fermi energy for clinically relevant markers.

FIGS. 7a and 7b show analytical curves obtained by plotting variation of the energy of the accessible interfacial states ($\Delta E$) at their fixed Fermi energy ($E_F$) for a range of clinically relevant markers. In particular, FIG. 7a shows analytical curves for C-reactive protein and α-synuclein (respectively markers for cardiac and general inflammation, and Parkinson's disease); FIG. 7b shows analytical curves for C-reactive protein and prostatic acid phosphatase (respectively markers for cardiac and general inflammation, and prostate cancer). The transduction principles active here are independent of specific film composition; the receptive films utilized are mixed thiolated ferrocene (providing the accessible responsive DOS) and thiolated alkyl or pegylated carboxylate. Assay sensitivity shows some predictable dependence on film. Error bars represent standard deviations derived from measurements conducted at three independent electrodes.

In all cases $\Delta N$ and/or $\Delta E$ remains a linear function of the logarithm of the target concentration (as noted previously that $\Delta E$[target]$\propto e^2/C_{\bar{\mu}}$[target] (variations rationalized in terms of the effective variation on the chemical energy state of the surface). Note that occupancy ($\Delta N$) or chemical potential/energy change ($\Delta E$) is most sensitive to target binding at potentials close to the Fermi level such that analytical curves ($\Delta E$ versus logarithm of [target]) can be derived by consideration of changes at this specific energy (FIG. 6b and FIG. 7).

The general principles of utilizing the resolved sensitivity of a surface confined electrode-chargeable DOS as a transducer signal of captured target can be extrapolated readily to antibody-modified non-redox active graphene derived interfaces assembled on metallic electrodes. In other words, the mesoscopic principles active at a redox-confined surface extend readily to non-redox active interfaces where an accessible DOS is confined to nanometre scale entities and accordingly highly responsive to environment. This is exemplified in FIG. 8a through the use of electrode immobilized and antibody modified reduced graphene oxide films.

FIG. 8a is a graph showing capacitance resolved variations in $\Delta E \propto \Delta 1/C_{\bar{\mu}}$ for electrochemically reduced graphene oxide multilayers functionalized with anti-CRP antibodies. FIG. 8b shows demonstrative selectivity obtained at microfabricated arrays modified with anti-CRP-modified redox-modified graphene oxide; here the response to $10^5$ pM CRP spiked into serum is shown relative to a that at native serum prior to spiking. FIG. 8c, equivalent to 8a, is the analytical curve comprising the linear relationship between and the logarithm of CRP concentration in serum as resolved at redox and graphene oxide modified micro-fabricated gold electrode arrays (detection limit 55 pM, linear analytical range is >$10^3$ pM and <$10^5$ pM, relevant to clinical need). In FIG. 8c the errors bars are standard deviations calculated across three measurements performed at the same disposable array.

Figure 8:
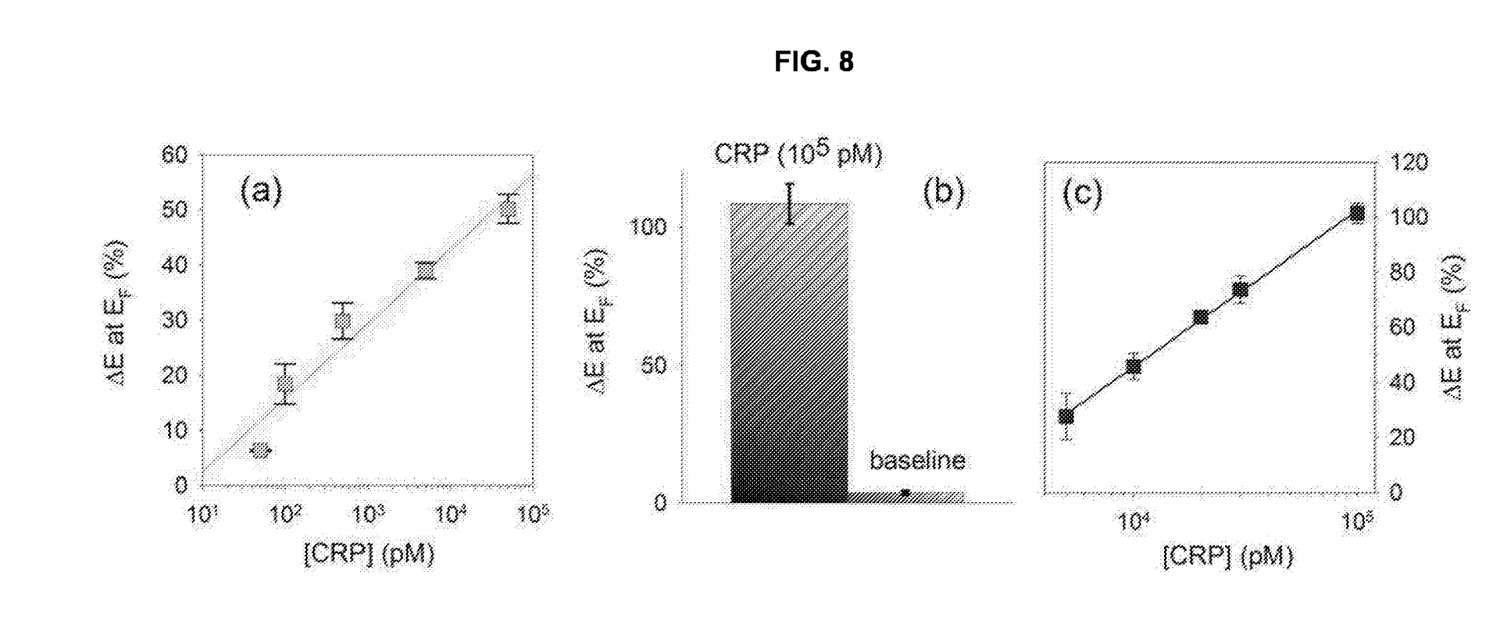
FIG. 8a shows capacitance resolved variations in energy for electrochemically reduced graphene oxide multilayers functionalised with anti-CRP antibodies.
FIG. 8b shows the demonstrative selectivity obtained at micro-fabricated arrays modified with anti-CRP-modified redox-modified graphene oxide.
FIG. 8c shows an analytical curve comprising the linear relationship between change in energy and the logarithm of CRP concentration in serum as resolved at redox and graphene oxide modified micro-fabricated gold electrode arrays.

It is now demonstrated that the operational principles associated with these capacitive spectroscopy resolved DOS assays are analogous to those operating in FET-based devices under equilibrium conditions (see FIG. 4c), wherein the quantum capacitance behaves in a manner equivalent to the channel states of FET devices. One first observes that the difference between the potential in the channel/bridge ($V_C$) and in the gate ($V_G$) is dependent on N as $V_C - V_G = -(eN/C_e)$ (in electro-active molecular layers this corresponds to the potential difference between the local potential of the accessible states and the external potential in the electrolyte). The gate capacitance is thus $dq/dV_G = (dq/dV_C)(dV_C/dV_G)$. By noting that $dq/dV_G$ is $C_{\bar{\mu}}$ and $dq/dV_C$ is the quantum capacitance ($C_q$), $dq/dV_G$ rearranges to give $$\frac{q^2}{C_{\bar{\mu}}} = q^2\left(\frac{dV_G}{dq}\right) = q^2\left(\frac{C_q + C_e}{C_e C_q}\right) = q^2\left(\frac{1}{C_e} + \frac{1}{C_q}\right) \quad (2)$$

an expression explicitly equivalent to Equation (1). Equation (2) implicitly demonstrates that, in experimentally accessing $C_{\bar{\mu}}$, the thermodynamic properties of the junctions are monitorable, potentially as a function of a neighbouring/integrated target recognition. This is accessible through $\Delta G = e^2/C_{\bar{\mu}} = -\kappa_B T \ln K_a$ which additionally implies the observed semi-logarithmic linear relationship (shown in FIGS. 6b, 7 and 8) resolved under equilibrium binding conditions. It is worth noting that these binding induced changes in electronic free energy are accompanied by associated change in state occupation (discharging/charging $C_{\bar{\mu}}$ and de-populating/populating states) such that the Fermi energy does not change (FIG. 5b). The capacitive DOS sensing introduced here is therefore similar to those operating in micro-fabricated FET devices but, significantly, is both highly chemically tailorable and requires just one contact; FIGS. 8a and 8c specifically show how the resolved electrochemical energy (electronically dominated) of an anti-CRP antibody functionalized reduced graphene oxide and composite interfaces responds to clinically relevant levels of CRP at macro-disk and micro-fabricated disposable electrode arrays.

It has therefore been shown by the disclosures herein that a surface confined and electronically addressable DOS (comprising either redox switchable centres or appropriately immobilized mesoscopic units) contributes to a readily resolved quantum capacitance. This charging reports on the occupancy of quantized states and responds sensitively to changes in local chemical potential. By appropriately introducing receptors this entirely reagentless sensing becomes highly specific and very sensitive. This transduction mechanism operates in a manner analogous to FET devices but in a markedly more experimentally accessible and chemically flexible manner.

With reference to FIGS. 4 to 8 above, it has therefore been shown that a change in the relaxation time (corresponding to a change in the capacitance of the sensor) is correlated with a change in the density of states. This concept is readily applicable to the sensor 100 of FIG. 1 in which the conductive connection is capacitively coupled to the mesoscopic probe element, and wherein an interaction between the mesoscopic probe element and a measurand of the environment affects the capacitance (and relaxation time) of the conductive connection. Although the effect on capacitance has been described herein, it should be appreciated that not only the capacitance will be affected by a detection event. Notably, the impedance and several other measurable quantities will likewise be affected, all of which are indicative of a change in the relaxation time.

Variations of the described embodiments are envisaged, for example, the features of all of the disclosed embodiments may be combined in any way and/or combination, unless such features are incompatible.

The mesoscopic probe element may be of any suitable form. For example, the mesoscopic probe element may be formed of any zero- (less than 10 nm), one- or two-dimensional compounds (providing that the others dimensions in the case of one- and two-dimensional compounds are below 10 nm). The mesoscopic probe element may comprise a metal oxide semiconductor, a mixed-valence semiconductor, an organic semiconductor, graphene, reduced graphene, fluorene, redox active polymers, or some other suitable material.

A conductive connection may be formed of any suitable electrically conductive material. For example, the conductive connection may comprise indium tin oxide (ITO), fluorine doped tin oxide (FTO), or a conductive carbonaceous compound such as graphene or glassy carbon. The conductive connection may comprise for example a metal such as gold, platinum, titanium, copper or a copper alloy.

The conductive connection or electrode or contact or body may comprise gold. They may comprise platinum. They may comprise Indium Tin Oxide (ITO). They may comprise Fluorine Doped Tin Oxide (FTO). They may comprise conductive polymers. They may comprise any other suitable conductor.

The mesoscopic probe element may comprise any suitable material, such as any mixed valence oxide, graphene oxide, or titanium dioxide. The mesoscopic probe element may comprise titanium nanotubes, for example.

Although only a handful of possible measurands have been described above, any measurand may be detected provided that there is a corresponding change in the density of states. For example, the sensor(s), sensing system(s) and sensing method(s) as described herein may be used to detect biological markers such as metabolytes or other small molecules and may be used to detect electromagnetic radiation. For example, the sensors, sensing systems and sensing methods disclosed herein may be used for the detection of disease marker proteins such as CRP, PAP, PSA, Insulin, HER2, Alpha-synuclein, CA19-9, or NS1. The sensors, sensing systems and sensing methods disclosed herein may be used for the detection of sugar molecules for glycoarrays, D-dimers, hormones, amino acids, alcohols, vitamins (such as B2 and B12), polyols, organic adds, nucleotides (for example inosine-5'-monophosphate and guanosine-5'-monophosphate), and so on. The skilled person would appreciate that the sensors, sensing systems and sensing methods disclosed herein may be used for the detection of a variety of measurands in a variety of settings.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A sensing method, comprising:
 providing a time-dependent electrical signal across a conductive connection between a first terminal and a second terminal of a sensor,
 the first terminal coupled with the second terminal via the conductive connection such that no biasing potential exists between the first and second terminals,
 the conductive connection quantum capacitively coupled to an environment via a density of states, DOS, sensitive mesoscopic probe element having an electroactive surface for exposure to the environment, the mesoscopic probe element having at least one dimension less than 15 nm and an accessible DOS that is quantum capacitively coupled to the conductive connection, wherein a quantum capacitance Cq varies as a function of the DOS occupancy of the mesoscopic probe element, wherein an interaction between the mesoscopic probe element and a measurand in the environment affects the DOS of the mesoscopic probe element, wherein the conductive connection having an associated resistive-capacitive relaxation time based on an capacitive property and an resistive property of the sensor;

receiving a time-dependent response signal from the sensor;

analysing the time-dependent response signal with respect to the time-dependent electrical signal;

determining, based on the analysis, a change in the relaxation time as a result of a change in the DOS of the mesoscopic probe element, wherein the change in the relaxation time is correlated with an interaction between the electroactive surface and the measurand of the environment.

2. The method according to claim 1, wherein the time-dependent electrical signal is an alternating current.

3. The method according to claim 1, wherein the time-dependent electrical signal is an electrical pulse.

4. The method according to claim 1, wherein analysing the time-dependent response signal with respect to the time-dependent electrical signal comprises determining a phase difference between the time-dependent response signal and the time-dependent electrical signal.

5. The method according to claim 4, wherein determining the change in the relaxation time comprises determining that a change in the relaxation time has occurred based on the phase difference.

6. The method according to claim 1, wherein analysing the time-dependent response signal with respect to the time-dependent electrical signal comprises determining an immittance function of the sensor from the time-dependent electrical signal and the time-dependent response signal.

7. The method according to claim 6, wherein analysing the time-dependent response signal with respect to the time-dependent electrical signal comprises determining the impedance of the sensor from the ratio of the time-dependent electrical signal to the time-dependent response signal.

8. The method according to claim 1, wherein analysing the time-dependent response signal with respect to the time-dependent electrical signal comprises determining the capacitance of the sensor using impedance-derived capacitance spectroscopy.

9. The method according to claim 1, further comprising determining a concentration of the measurand in the environment.

10. The method according to claim 1, wherein the interaction between the electroactive surface and the measurand comprises an electronic interaction.

11. The method according to claim 1, wherein the interaction between the electroactive surface and the measurand comprises a molecular binding event.

12. The method according to claim 1, wherein the interaction between the electroactive surface and the measurand comprises a photon-electron interaction.

13. The method according to claim 1, wherein the mesoscopic probe element comprises graphene oxide or titanium dioxide or a mixed valence oxide.

14. The method according to claim 1, wherein the at least one dimension is less than or equal to 10 nanometres.

15. The method according to claim 1, wherein the conductive connection comprises gold.

16. The method according to claim 1, wherein the electroactive surface of the mesoscopic probe element is an exposed surface.

* * * * *